(12) United States Patent
Beus et al.

(10) Patent No.: US 9,387,215 B2
(45) Date of Patent: Jul. 12, 2016

(54) ANIMAL FEED INCLUDING CATIONIC CHOLESTEROL ADDITIVE AND RELATED METHODS

(71) Applicants: Chad S. Beus, Spanish Fork, UT (US); Paul B. Savage, Mapleton, UT (US)

(72) Inventors: Chad S. Beus, Spanish Fork, UT (US); Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 14/257,776

(22) Filed: Apr. 21, 2014

(65) Prior Publication Data

US 2014/0315873 A1 Oct. 23, 2014

Related U.S. Application Data

(60) Provisional application No. 61/814,816, filed on Apr. 22, 2013.

(51) Int. Cl.
*A61K 31/575* (2006.01)
*A23K 1/165* (2006.01)
*A23K 1/16* (2006.01)
*A23K 1/18* (2006.01)

(52) U.S. Cl.
CPC .............. *A61K 31/575* (2013.01); *A23K 1/165* (2013.01); *A23K 1/1646* (2013.01); *A23K 1/184* (2013.01); *A23K 1/1806* (2013.01); *A23K 1/1813* (2013.01); *A23K 1/1826* (2013.01); *A23V 2002/00* (2013.01)

(58) Field of Classification Search
CPC .................................................. A61K 31/575
See application file for complete search history.

(56) References Cited

U.S. PATENT DOCUMENTS 4,661,341 A 4/1987 Benedict et al.
4,842,593 A 6/1989 Jordan et al.
(Continued)

FOREIGN PATENT DOCUMENTS

CN 101378761 3/2009
CN 102172356 9/2011
(Continued)

OTHER PUBLICATIONS

Van den Bogaard et al.; "Antibiotic Usage in Animals: Impact on Bacterial Resistance and Public Health"; 1999; Drugs; 58 (4): 589-607.*

(Continued)

*Primary Examiner* — Timothy Thomas
(74) *Attorney, Agent, or Firm* — Workman Nydegger

(57) ABSTRACT

Methods and feed compositions for increasing health of agricultural animals include administering a cationic cholesterol additive through the diet of the animal, such as through solid feed or drinking water of the animals. The method includes feeding an animal a diet comprised of a cationic cholesterol additive, such as a compound with a sterol backbone and a plurality of cationic groups attached thereto. The feed composition may include a solid or liquid feed component and a cationic cholesterol additive. The methods and compositions are useful for animals raised in confined feed operations, such as cattle, swine, horses, sheep, or poultry, and can reduce harmful bacteria in the digestive tract, increase beneficial bacteria flora, improve feed conversion efficiency, reduce morbity and/or mortality, and/or yield harvested meat having reduced content of harmful bacteria.

22 Claims, 3 Drawing Sheets

(56) References Cited

U.S. PATENT DOCUMENTS

| | | |
|---|---|---|
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,380,839 A | 1/1995 | McCall et al. |
| 5,552,057 A | 9/1996 | Hughes et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,350,738 B1 | 2/2002 | Savage et al. |
| 6,486,148 B2 | 11/2002 | Savage et al. |
| 6,562,318 B1 | 5/2003 | Filler |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 9/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 2002/0091278 A1 | 7/2002 | Savage et al. |
| 2003/0099717 A1 | 5/2003 | Cabrera |
| 2004/0009227 A1 | 1/2004 | Yao |
| 2004/0058974 A1 | 3/2004 | Courtney et al. |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0324517 A1 | 12/2009 | Kline |
| 2010/0330086 A1 | 12/2010 | Savage et al. |
| 2011/0091376 A1 | 4/2011 | Savage |
| 2011/0123624 A1 | 5/2011 | Zasloff |
| 2012/0088733 A1 | 4/2012 | Kim et al. |
| 2012/0107382 A1 | 5/2012 | Savage et al. |
| 2013/0022651 A1 | 1/2013 | Savage |
| 2013/0053507 A1 | 2/2013 | Savage |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0271761 A1 | 9/2014 | Savage et al. |
| 2014/0274913 A1 | 9/2014 | Savage et al. |
| 2014/0369941 A1 | 12/2014 | Vazquez et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |

FOREIGN PATENT DOCUMENTS

| | | | |
|---|---|---|---|
| EP | EP 0341951 | 11/1989 | |
| EP | 1208844 | 5/2002 | |
| JP | 02014741 | 1/1990 | |
| JP | 06153779 | 6/1994 | |
| JP | 07501826 | 2/1995 | |
| JP | 09248454 | 9/1997 | |
| JP | 2002505292 | 2/2002 | |
| JP | 2002255771 | 9/2002 | |
| JP | 2002534532 | 10/2002 | |
| JP | 2002538093 | 11/2002 | |
| JP | 2004506645 | 3/2004 | |
| JP | 2010533051 | 10/2010 | |
| JP | 2010538074 | 12/2010 | |
| JP | 2011527702 | 11/2011 | |
| JP | 2014500741 | 1/2014 | |
| WO | WO 95024415 | 9/1995 | |
| WO | WO 9944616 | 9/1999 | |
| WO | WO 0042058 | 7/2000 | |
| WO | WO 0214342 | 2/2002 | |
| WO | WO02067979 | 9/2002 | |
| WO | WO 03015757 | 2/2003 | |
| WO | WO 03090799 | 11/2003 | |
| WO | WO2004082588 | 9/2004 | |
| WO | WO 2004112852 | 12/2004 | |
| WO | WO 2007089903 | 8/2007 | |
| WO | WO 2007089906 | 8/2007 | |
| WO | WO 2007089907 | 8/2007 | |
| WO | WO 2007089907 A2 * | 8/2007 | ............ A61K 31/56 |
| WO | WO 2007134176 | 11/2007 | |
| WO | WO 2008038965 | 4/2009 | |
| WO | WO 2009079066 | 6/2009 | |
| WO | WO2010006192 | 1/2010 | |
| WO | WO 2010036427 | 4/2010 | |
| WO | WO 2010062562 | 6/2010 | |
| WO | WO2011066260 | 6/2011 | |
| WO | WO 2011109704 | 9/2011 | |
| WO | WO 2012061651 | 5/2012 | |
| WO | WO 2013029055 | 2/2013 | |
| WO | WO 2013029059 | 2/2013 | |
| WO | WO 2013109236 | 7/2013 | |

OTHER PUBLICATIONS

Guan et al.; "Preparation and Characterization of Cholic Acid-Derived Antimicrobial Agents with Controlled Stabilities"; 2000; Organic Letters; 2(18): 2837-2840.*

Suzuki et al.; "Molecular Genetics of Plant Sterol Backbone Synthesis"; 2007; Lipids; 42: 47-54.*

U.S. Appl. No. 13/783,007, filed Mar. 1, 2013, Savage.

U.S. Appl. No. 14/339,342, filed Jul. 23, 2014, Vazquez et al.

U.S. Appl. No. 14/341,304, filed Jul. 25, 2014, Savage et al.

U.S. Appl. No. 14/364,283, filed Jul. 29, 2014, Vazquez et al.

U.S. Appl. No. 14/398,094, filed Oct. 30, 2014, Savage et al.

U.S. Appl. No. 14/515,858, filed Oct. 16, 2014, Savage et al.

Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999, pp. 1865-1868, XP004155984, ISSN: 0040-4039, DOI: 10.1016/S0040-4039(99)00075-1.

Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.

Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Ding, et al., "Origins of cell selectivity of cationic steroid antibiotics", Journal of American Chemical Society, Oct. 2004, pp. 13642-13648.

(56) References Cited

OTHER PUBLICATIONS

Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Supporting Information: Preparation and Characterization of Cholic Acid-Derived Antimicrobial Agents with Controlled Stabilities", Organic Letters, Aug. 17, 2000, pp. 1-7, XP55017313, Retrieved from the Internet: URL:http://pubs.acs.org/doi/suppl/10.1021/o10062704/suppl file/o10062704 sl.pdf.
International Search Report for PCT Application No. PCT/US2009/0475485 dated Feb. 17, 2010.
International Search Report for PCT Application No. PCT/US2011/059225 dated Jan. 31, 2012.
International Search Report for PCT Application No. PCT/US2012/047750, Mailed Date: Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, Mailed Date: Jul. 24, 2013.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Steeneveld, et al., "Cow-specific treatment of clinical mastitis: an economic approach", Journal of Dairy Science vol. 94, Jan. 2011, pp. 174-188.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/000,010, filed Dec. 17, 2012, Restriction Requirement dated Dec. 4, 2012.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.
U.S. Appl. No. 13/288,902, filed Nov. 3, 2011, Notice of Allowance dated Aug. 9, 2013.
U.S. Appl. No. 13/783,131, filed Mar. 1, 2013, Office Action dated Oct. 23, 2014.
U.S. Appl. No. 14/056,122, filed Oct. 17, 2013, Office Action dated Sep. 3, 2014.
U.S. Appl. No. 14/288,126, filed May 27, 2014, Savage, et al.
P. B. Savage, et al., "Thin Films Containing Ceragenins Prevent Biofilm Formation on Endotracheal Tubes", 9th International Federation of Infection Control Congress, Oct. 14, 2008, pp. 1-1.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

Savage, et al., "Antibacterial Activities of Thin Films Containing Ceragenins", Microbial Surfaces: Structure, Interactions and Reactivity, ACS, May 30, 2008, pp. 65-78.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
K. Leszczynska et al., "Potential of ceragin CSA-13 and its mixture with pluronic F-127 as treatment of topical bacterial infections", Journal of Applied Microbiology, vol. 110, No. 1, Oct. 21, 2010, pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
International Search Report for PCT Application No. PCT/US2012/047750, Mailed Date: Oct. 5, 2012, filed Sep. 27, 2012, 3 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
U.S. Appl. No. 13/554,957, filed Apr. 1, 2014, Office Action.
U.S. Appl. No. 13/554,957, filed Aug. 1, 2014, Notice of Allowance.
U.S. Appl. No. 13/594,608, filed Jan. 30, 2014, Office Action.
U.S. Appl. No. 13/594,612, filed May 15, 2014, Office Action.
U.S. Appl. No. 13/615,324, filed Jan. 30, 2014, Office Action.
U.S. Appl. No. 13/554,930, filed Jul. 11, 2014, Office Action.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
U.S. App. No. 13/615,244, filed Sep. 13, 2012, Office Action dated Jan. 16, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/694,028, filed Apr. 23, 2015, Beus et al.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/873,013, filed Oct. 1, 2015, Savage et al.
U.S. Appl. No. 14/926,738, filed Oct. 29, 2015, Vazquez et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/830,356, filed Aug. 19, 2015, Savage.
U.S. Appl. No. 14/886,213, filed Sep. 25, 2015, Savage.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 20.
International Search Report for PCT Application No. PCT/US2013/065510 dated Apr. 30, 2015.

(56) References Cited

OTHER PUBLICATIONS

International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Zanger et al., "Structure-Activity Relationship and Drug Design", Remington's Pharmaceutical Sciences, Chapter 27, 16th Edition, 1980, pp. 420-425.

\* cited by examiner

ANIMAL FEED INCLUDING CATIONIC CHOLESTEROL ADDITIVE AND RELATED METHODS

CROSS-REFERENCE TO RELATED APPLICATIONS

This application claims the benefit of U.S. Provisional Application No. 61/814,816, filed Apr. 22, 2013, the disclosure of which is incorporated herein in its entirety.

BACKGROUND OF THE INVENTION

1. The Field of the Invention

The invention relates to compositions and methods for improving the health, such as improved health of the digestive tract, and reducing the morbidity of animals, such as those raised for food, including, but not limited to, animals raised in confined animal feed operations.

2. The Relevant Technology

The U.S. has developed a very efficient and sophisticated system for producing meat, milk, poultry, and egg products involving concentrated animal feeding operations (CAFOs) in order to insure the sustainability of America's food supply. Confinement of large numbers of animals can, however, lead to difficulties in maintaining the animals healthy. The use of antibiotics and growth hormones to reduce illness and increase meat and animal product production is widespread. There is growing pressure on the industry to eliminate the use of antibiotics and growth hormones. This effort has been met with little success, primarily due to the increased morbidity and weight loss that occurs in CAFOs when antibiotics such as tetracycline are eliminated.

SUMMARY

Disclosed herein are animal feed compositions and methods for improving animal health that include and/or use a cationic cholesterol additive which enhances the health and survival of animals used for food production. Unlike conventional antibiotics given to animals, the cationic cholesterol additives disclosed herein have been found to promote the production of beneficial microflora, which improves the health of an animal's digestive tract, resulting in reduced morbidity and increased weight gain. Healthier animals treated using the compositions and methods disclosed herein are able to maximize their natural ability to grow and produce healthy food products. The cholesterol additive has little or no bioavailability, which means the additive passes through the digestive (e.g., gastrointestinal) tract of the animal without significantly affecting the animal. The lack of bioavailability is advantageous because it prevents the additive from being incorporated into the animal, where it could possibly be ingested by a person eating the animal or animal product and allows products from the animals to be substantially free of the cationic cholesterol additive.

Improved health of agricultural animals is achieved by periodically administering a cationic cholesterol additive to an animal during its growth. The cholesterol additives include a sterol backbone and a plurality of cationic groups attached thereto. The additive is delivered orally to the animal in the animal's feed. The feed can be a solid or liquid composition and can include any alimentary substance used to sustain an animal, including but not limited to solid ingestibles, liquid ingestibles, and drinking water of the animal. Examples of suitable feed components into which the cationic cholesterol additive may be mixed include, but are not limited to, proteins, carbohydrates, fats, minerals, fiber, or water.

The mechanism of action for the increased health and reduced morbidity is presently being studied. While the present invention is not limited to any particular mechanism, it is believed that the reduced morbidity and improved health in animals consuming the feed and treated according to the methods described herein is the result of increases in the microbial competitiveness of beneficial micro-flora ordinarily found in healthy animals, such as *Lactobacillus* bacteria. Unlike traditional antibiotics, the cationic cholesterol additives used in the feed and methods described herein do not inhibit the growth of *lactobacillus*, which can more easily out-compete harmful bacteria that lead to infection and morbidity in animals raised in CAFOs. This results in healthier animals with healthier micro-flora of the digestive tract.

It is believed that increased health may be akin to the use of probiotics, which can positively affect the relative balances of beneficial and harmful flora. However, because the cationic additives of the present invention are not living, they can be included more easily in the feed in smaller concentrations as compared to other types of probiotics while achieving higher effective rates.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

DETAILED DESCRIPTION

I. Definitions

Figure 1:
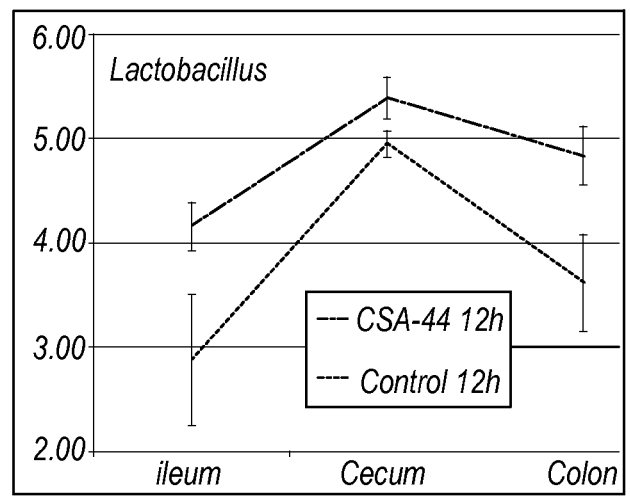
FIG. 1 is a graph showing the effect of CSA-44 on beneficial bacterial flora in the digestive tract of mice.

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

The term "ring" as used herein can be heterocyclic or carbocyclic. The term "saturated" used herein refers to a fused ring having each atom in the fused ring either hydrogenated or substituted such that the valency of each atom is filled. The term "unsaturated" used herein refers to a fused ring where the valency of each atom of the fused ring may not be filled with hydrogen or other substituents. For example, adjacent carbon atoms in the fused ring can be doubly bound to each other. Unsaturation can also include deleting at least one of the following pairs and completing the valence of the ring carbon atoms at these deleted positions with a double bond; such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO$ $(CH_2)_mO$—, $R^b(CH_2)_nO$—, $R^cC(O)O(CH_2)_pO$—, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multicyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multicyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys includes methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a —CN group.

A "carbonyl" or an "oxo" group refers to a C═O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(═O)O-alkyl- and alkyl-O—C(═O)-alkyl- with the term alkyl as defined herein.

As used herein, "C-carboxyalkyl" refers to a carboxy group connected, as a substituent, to an alkyl group. Examples include HO—(C═O)-alkyl, with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

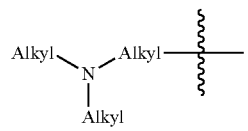

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(═O)O— and H$_2$N-alkyl-O—C(═O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl -NH—C(═O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(═O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

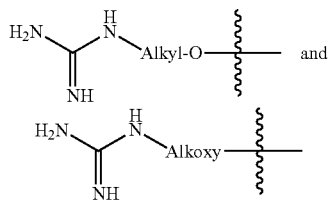

and with the terms "alkyl" and "alkoxy" as defined herein.

As used herein, "guanidinoalkylcarboxy" refers to a guanidinyl group connected, as a substituent, to an alkyl group connected, as a substituent, to a carboxy group. Examples include

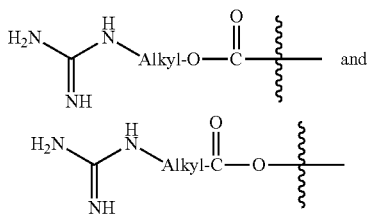

with the term "alkyl" as defined herein.

As used herein, "quaternary ammonium alkylcarboxy" refers to a quaternized amino group connected, as a substituent, to an alkyl group connected, as a substituent, to a carboxy group. Examples include

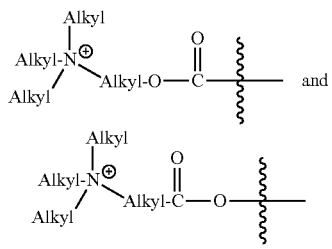

with the term "alkyl" as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and nor-leucine.

A linking group is a divalent moiety used to link one steroid to another steroid. In some embodiments, the linking group is used to link a first compound with a second compound (which may be the same or different). An example of a linking group is $(C_1\text{-}C_{10})$ alkyloxy-$(C_1\text{-}C_{10})$ alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl,tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure Compounds may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$. A tail moiety may include the heteroatom (O or N) covalently coupled to the sterol backbone. The tail moiety may, for example, be configured to alter the hydrophobicity/hydrophilicity of the compound. Compounds of the present disclosure having different degrees of hydrophobicity/hydrophilicity may, for example, have different rates of uptake into different target microbes. Likewise, altering the hydrophobicity/hydrophilicity of the compounds described herein may affect the retention of the CSA compounds in certain media.

II. Feed Components

The feed can include any number of components typical of animal feeds. Examples of suitable feed components include, but are not limited to proteins, carbohydrates, fats, minerals, fiber, feed water, and additional additives.

The feed can include a percentage of protein that ensures healthy growth of an animal. Examples of suitable types of proteins that can be included in the feed include, but are not limited to, meat scraps (lysine), fish meal (lysine, methionine), poultry byproduct meal (tryptophan, lysine), blood meal, liver and glandular meal, feather meal (hydrolyzed), animal tankage, milk products, cottonseed meal, peanut meal, soybean meal, sesame meal, sunflower seed meal.

Carbohydrates are necessary to provide animals with the energy required to grow. Examples of suitable carbohydrates include, but are not limited to, starch, cellulose, pentosans, and other complex carbohydrates. Carbohydrates can be obtained from corn, sorghum grains (milo), barley, rye, oats, wheat, wheat middlings, and various grain by-products.

Fats may also be included. Most feed ingredients (maize, barley, safflower, milo, wheat, rice, bran, etc.) contain approximately 2-5% fat and linoleic acid, which are often required for agricultural animals or else they will grow poorly, have a higher tendency to accumulate liver fat, and be more susceptible for respiratory infection. Sources of fats include animal tallow (beef), lard, corn oil, and other vegetable oils.

Minerals used in animal feeds typically include calcium, phosphorus, sodium, potassium, magnesium, chlorine, iodine, iron, manganese, copper, molybdenum, zinc and selenium. Common mineral supplements in poultry feed are: Limestone, Bone meal, Oyster shell, Sodium chloride, Dicalcium phosphate, Manganese sulphate, Potassium iodide, and Superphosphate. Sources of minerals include meat scraps, fish meal, milk products, ground limestone (calcium), ground oyster shells (calcium), dicalcium phosphate (calcium, phosphorus), defluorinated rock phosphate (phosphorus, calcium), steamed bone meal (phosphorus, calcium), salt (sodium, chlorine, iodine), manganese sulfate (manganese), manganese oxide (manganese), zinc carbonate (zinc), zinc oxide (zinc).

Animal feeds can include vitamins. Vitamins most commonly function as coenzymes and regulators of metabolism. Example sources include yeasts, fish solubles, distillers' solubles, liver meal, alfalfa meal, milk by-products.

In addition to the cationic cholesterol additive, the feed can include other additional feed additives. Some additives that promote feed intake or selection include antioxidants like BHT (Butylated hydroxytoluene), Santoquin, Ethoxyquin, BHA (Butylated hydroxyanisode), and DPPD (Diphenyl paraphenyl diamine. Pellet binders include Sodium Bentonite (clay), liquid or solid by-products of the wood pulp industry, molasses, and guarmeal. Additives that enhance the color or quality of the marketed product include Xanthophylls, synthetic carotinoid, and canthaxanthin. Chelates include EDTA. Enzymes include Agrozyme, Diazyme, Zymopabst, Prozyme and Avizyme. Probiotics are typically strains of *lactobacillus* and *streptococcus*. While most traditional animal feeds include an antibiotic such as penicillin, streptomycin, tetracyclines, or aureomycin, in a preferred embodiment, the feed of the present invention is free of penicillin, streptomycin, tetracycline, aureomycin, derivatives of these, and similar compounds that inhibit bacterial growth and in particular is free of antibiotics that inhibit protein synthesis. The cationic cholesterol additive allows the feed and/or animals to be grown free of these compounds while still achieving good growth and health. Although not necessary or preferred the feed and methods of the present invention can include antibiotics.

Those skilled in the art are familiar with the particular recipes for making feed for particular types of agricultural animals and can be prepared in similar formulations when adding an effective amount of the cationic cholesterol additive.

The feed may be liquid or solid. Examples of cholesterol feed compositions include embodiments where the cationic cholesterol group is the primary component of feed water (i.e., water provided to the animal for oral consumption by the animal).

III. Cationic Cholesterol Additives

Cationic cholesterol compounds useful as cationic cholesterol additives in accordance with this disclosure are described herein, both generically and with particularity, and also in U.S. Pat. Nos. 6,350,738, 6,486,148, 6,767,904, 7,598,234, and 7,754,705, which are incorporated herein by reference. Compounds include cholesterol derivatives that exhibit one or more beneficial alimentary effects or functions when consumed orally by agricultural animals.

The cationic cholesterol additives are synthetically produced small molecules that include a sterol backbone having various charged groups (e.g., amine and cationic groups) attached to the sterol backbone. The backbone can be used, for example, to orient amine or guanidine groups on one face, or plane, of the sterol backbone.

The cholesterol additives can be cationic and amphiphilic, based upon the functional groups attached to the backbone. They can be facially amphiphilic with a hydrophobic face and a polycationic face. For example, a scheme showing a compound having primary amino groups on one face, or plane, of a backbone is shown below in Scheme I:

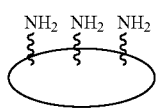

Scheme I

The charged groups and amphiphilic properties are believed to be responsible for observed selective inhibition of undesired or harmful bacterial while maintaining or enhancing growth of beneficial microflora in the digestive (e.g., gastrointestinal) tract.

In some embodiments, the cholesterol additive may have a formula as set forth in Formula (I), or a salt thereof:

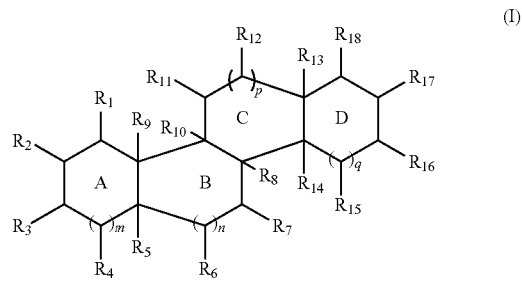

where m, n, p, and q are independently 0 or 1; $R^1$-$R^{18}$ represent substituents that are attached to the indicated atom on the steroid backbone (i.e., steroid group); and at least two, preferably at least three, of $R^1$-$R^{18}$ each include a cationic group.

In one embodiment, rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N$—$HC(Q_5)$-$C(O)$—O—, $H_2N$—$HC(Q_5)$-$C(O)$—$N(H)$—, a substituted or unsubstituted azidoalkyloxy, a substituted or unsubstituted cyanoalkyloxy, P.G.-HN—$HC(Q_5)$-$C(O)$—O—, a substituted or unsubstituted guanidinoalkyloxy, a substituted or unsubstituted quaternary ammonium alkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, azidoalkyloxy, cyanoalkyloxy, P.G.-HN—$HC(Q_5)$-$C(O)$—O—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a quaternary ammonium alkylcarboxy, a substituted or unsubstituted di(alkyl)aminoalkyl, $H_2N$—$HC(Q_5)$-$C(O)$—O—, $H_2N$—$HC(Q_5)$-$C(O)$—$N(H)$—, azidoalkyloxy, cyanoalkyloxy, P.G.-HN—$HC(Q_5)$-$C(O)$—O—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino-($C_1$-$C_{22}$) alkylamino, a substituted or unsubstituted ($C_1$-$C_{22}$) aminoalkyl, a substituted or unsubstituted aryl, a substituted or unsubstituted arylamino-($C_1$-$C_{22}$) alkyl, a substituted or unsubstituted ($C_1$-$C_{22}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkyloxy-($C_1$-$C_{22}$) alkyl, a substituted or unsubstituted ($C_1$-$C_{22}$)aminoalkylcarboxy, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted di($C_1$-$C_{22}$ alkyl)aminoalkyl, $H_2N$—$HC(Q_5)$-$C(O)$—O—, $H_2N$—$HC(Q_5)$-$C(O)$—$N(H)$—, a substituted or unsubstituted ($C_1$-$C_{22}$) azidoalkyloxy, a substituted or unsubstituted ($C_1$-$C_{22}$) cyanoalkyloxy, P.G.-HN—$HC(Q_5)$-$C(O)$—O—, a substituted or unsubstituted ($C_1$-$C_{22}$) guanidinoalkyloxy, a substituted or unsubstituted ($C_1$-$C_{22}$) quaternary ammonium alkylcarboxy, and a substituted or unsubstituted ($C_1$-$C_{22}$) guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) aminoalkyl, a substituted or unsubstituted aryl, a substituted or unsubstituted ($C_1$-$C_{22}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted di($C_1$-$C_{22}$ alkyl)aminoalkyl, $H_2N$—$HC(Q_5)$-$C(O)$—O—, $H_2N$—$HC(Q_5)$-$C(O)$—$N(H)$—, a substituted or unsubstituted ($C_1$-$C_{22}$) azidoalkyloxy, a substituted or unsubstituted ($C_1$-$C_{22}$) cyanoalkyloxy, P.G.-HN—$HC(Q_5)$-$C(O)$—O—, a substituted or unsubstituted ($C_1$-$C_{22}$) guanidinoalkyloxy, and ($C_1$-$C_{22}$) guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{22}$) aminoalkyl, a substituted or unsubstituted ($C_1$-$C_{22}$) aminoalkyloxy, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino ($C_1$-$C_{22}$) alkylamino, a substituted or unsubstituted ($C_1$-$C_{22}$) aminoalkylcarboxy, a substituted or unsubstituted arylamino ($C_1$-$C_{22}$) alkyl, a substituted or unsubstituted ($C_1$-$C_{22}$) aminoalkyloxy ($C_1$-$C_{22}$) aminoalkylaminocarbonyl, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted ($C_1$-$C_{22}$) quaternary ammonium alkylcarboxy, a substituted or unsubstituted di($C_1$-$C_{22}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{22}$) azidoalkyloxy, a substituted or unsubstituted ($C_1$-$C_{22}$) cyanoalkyloxy, P.G.-HN—HC($Q_5$)-C(O)—O—, a substituted or unsubstituted ($C_1$-$C_{22}$) guanidinoalkyloxy, and a substituted or unsubstituted ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkyl amino-($C_1$-$C_{18}$) alkylamino, ($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino -($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted aryl amino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_{11}$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino -($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, the compounds, or pharmaceutically acceptable salts thereof, are selected from the compound of Formula (IA), which is a subgenus of Formula (I) in that $R_{15}$ is omitted:

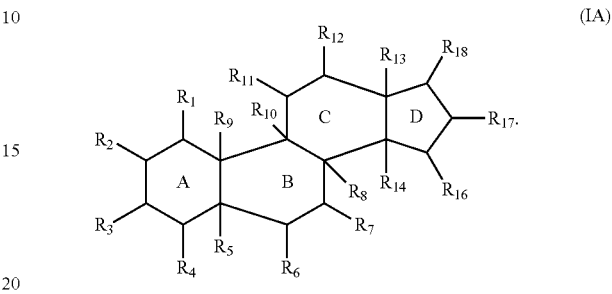

(IA)

wherein fused rings A, B, C, and D are independently saturated or fully or partially unsaturated; and each of $R_1$ through $R_4$, $R_6$, $R_7$, $R_{11}$, $R_{12}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, $C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, a substituted or unsubstituted C-carboxy($C_1$-$C_{10}$)alkyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternary ammonium alkylcarboxy, and ($C_1$-$C_{10}$) guanidinoalkyl carboxy, where $Q_5$ is a side chain of any amino acid (including the side chain of glycine, i.e., H), PG. is an amino protecting group, and $R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, 10 a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, $C_1$-$C_{10}$ haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and ($C_1$-$C_{10}$) guanidinoalkylcarboxy, where $Q_5$ is a side chain of any amino acid, PG. is an amino protecting group, and provided that at least two of $R_1$ through $R_{14}$ are independently selected from the group consisting of a substituted or unsubstituted ($C_1$-$C_{10}$) aminoalkyloxy, ($C_1$-$C_{10}$) alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino$(C_1-C_{10})$ alkyl, a substituted or unsubstituted $(C_1-C_{10})$ aminoalkyloxy-$(C_1-C_{10})$ alkyl, a substituted or unsubstituted $(C_1-C_{10})$ aminoalkylaminocarbonyl, $(C_1-C_{10})$ quaternary ammonium alkylcarboxy, $H_2N$—$HC(Q_5)C(O)$—$O$—, $H_2N$—$HC(Q_5)$-$C(O)$—$N(H)$—, $(C_1-C_{10})$ azidoalkyloxy, $(C_1-C_{10})$ cyanoalkyloxy, PG.-HN—$HC(Q_5)$-$C(O)$—$O$, $(C_1-C_{10})$ guanidinoalkyloxy, and $(C_1-C_{10})$ guanidinoalkylcarboxy; or a pharmaceutically acceptable salt thereof.

In some embodiments, rings A, B, C, and D are independently saturated, heterocyclic, and/or non-heterocyclic.

In some embodiments, $R_3$, $R_7$, $R_{12}$, and $R_{18}$ are independently selected from the group consisting of hydrogen, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino-$(C_1-C_{18})$ alkylamino, an unsubstituted $(C_1-C_{18})$ aminoalkyl, an unsubstituted arylamino-$(C_1-C_{18})$ alkyl, an unsubstituted $(C_1-C_{18})$ aminoalkyloxy, an unsubstituted $(C_1-C_{18})$ aminoalkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, an unsubstituted C-carboxy$(C_1-C_{18})$alkyl, unsubstituted $(C_1-C_{18})$ guanidinoalkyloxy, unsubstituted $(C_1-C_{18})$ quaternary ammonium alkylcarboxy, and unsubstituted $(C_1-C_{18})$ guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same substituent or different substituents and/or may be independently an aminoalkyloxy and/or an aminoalkylcarboxy. In some embodiments, $R_{18}$ is alkylaminoalkyl, alkoxycarbonyl-alkyl, di(alkyl)aminoalkyl, C-carboxyalkyl, or an alkylcarboxyalkyl. In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-$(C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

In some embodiments, the compounds or salts thereof are selected from the compound of Formula (IB), which is a subgenus of Formula (IA):

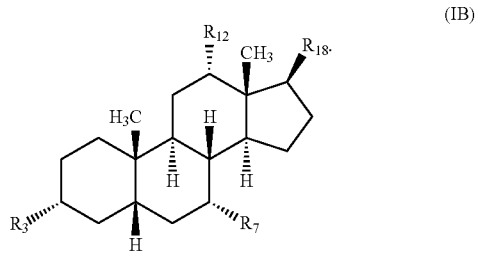

In some embodiments, the compounds or salts thereof of the compound of Formula (IB), is selected from the group consisting of:

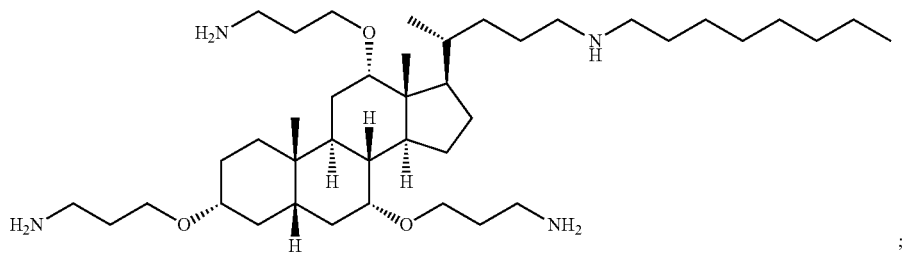

;

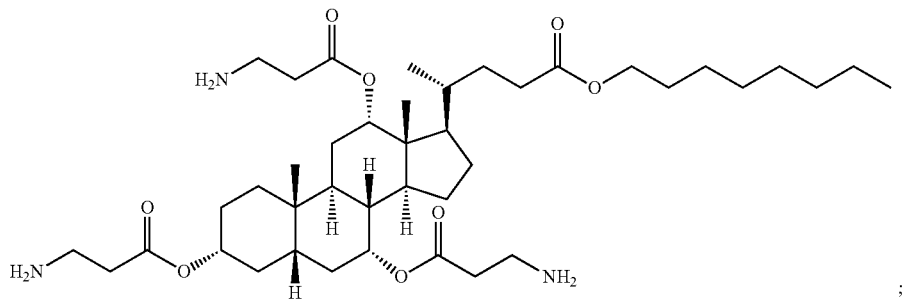

;

-continued
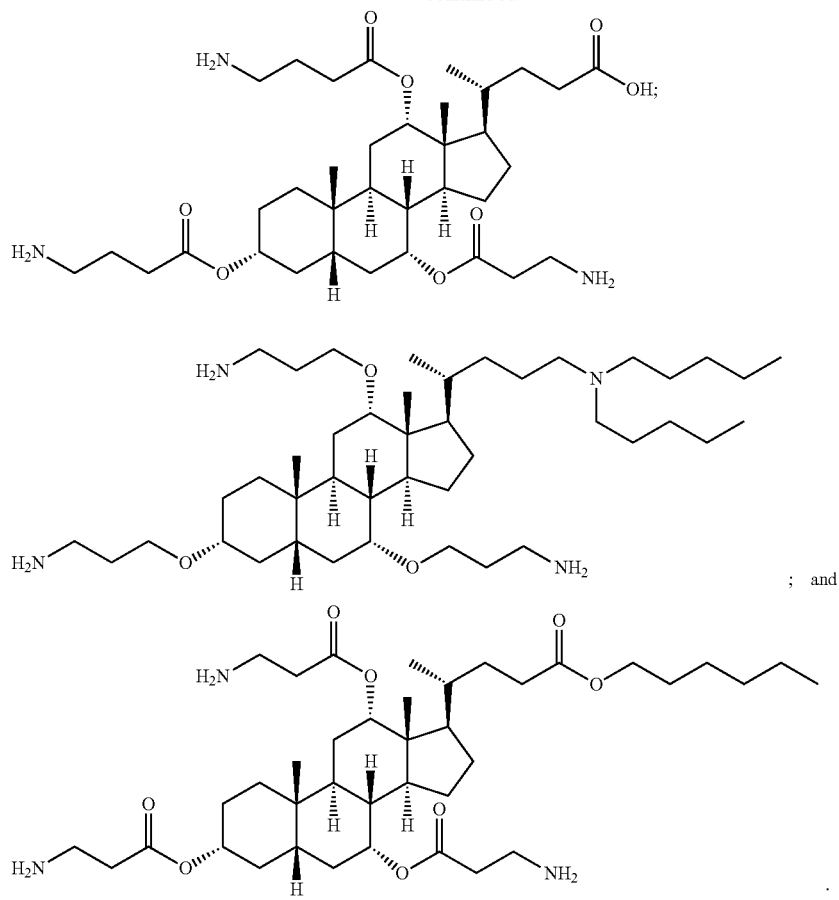
In some embodiments, the cholesterol additive is
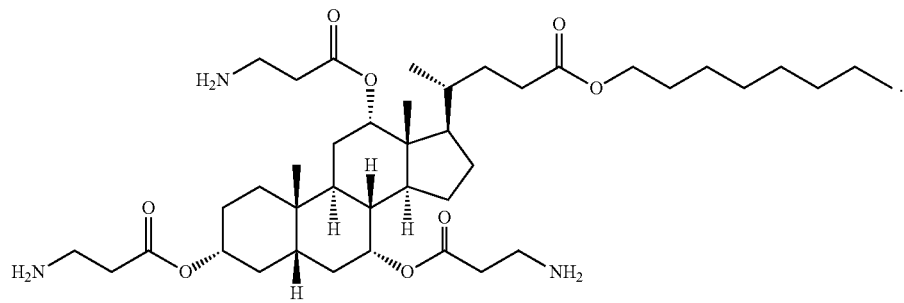
In some embodiments, the cholesterol additive is
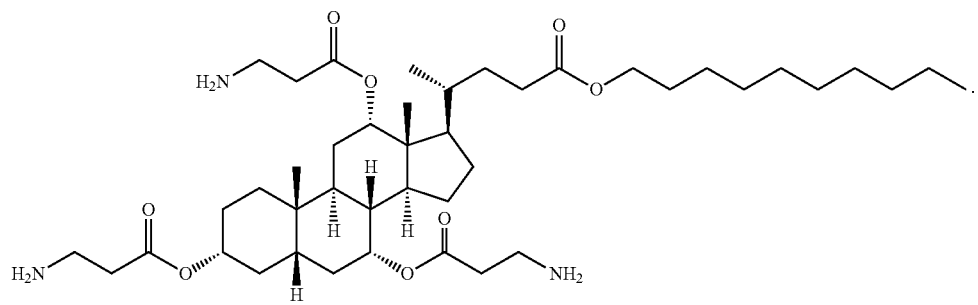

In some embodiments, the cholesterol additive is
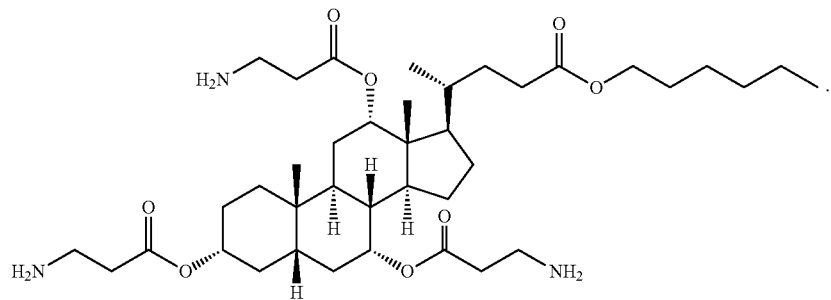
In some embodiments, the cholesterol additive is
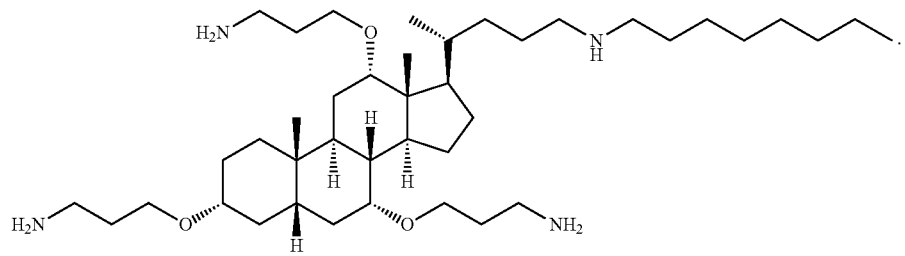
In some embodiments, the cholesterol additive is
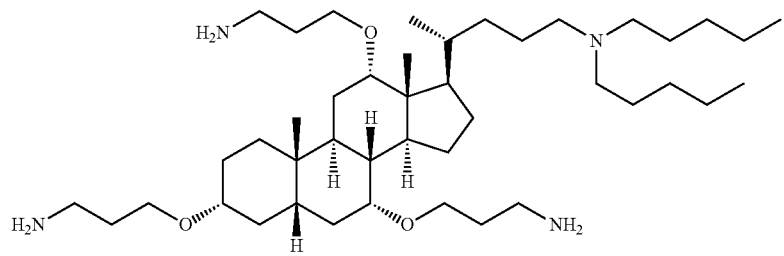
In some embodiments, the cholesterol additive is
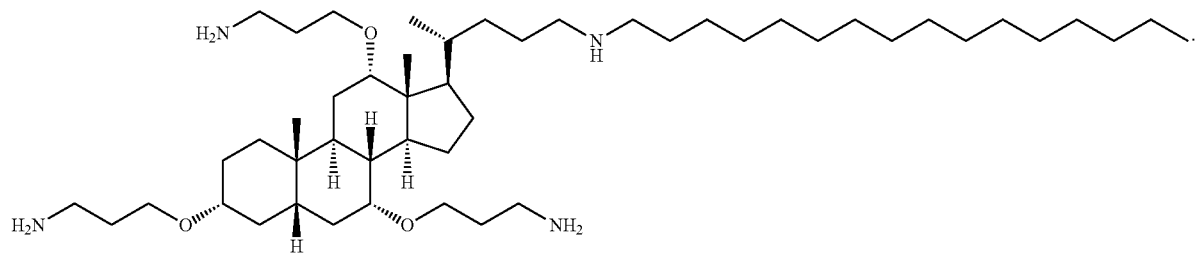
In some embodiments, the cholesterol additive is
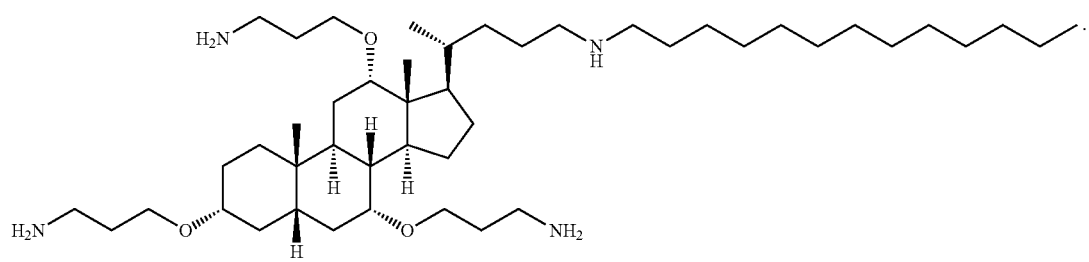

In some embodiments, the cholesterol additive is selected from:
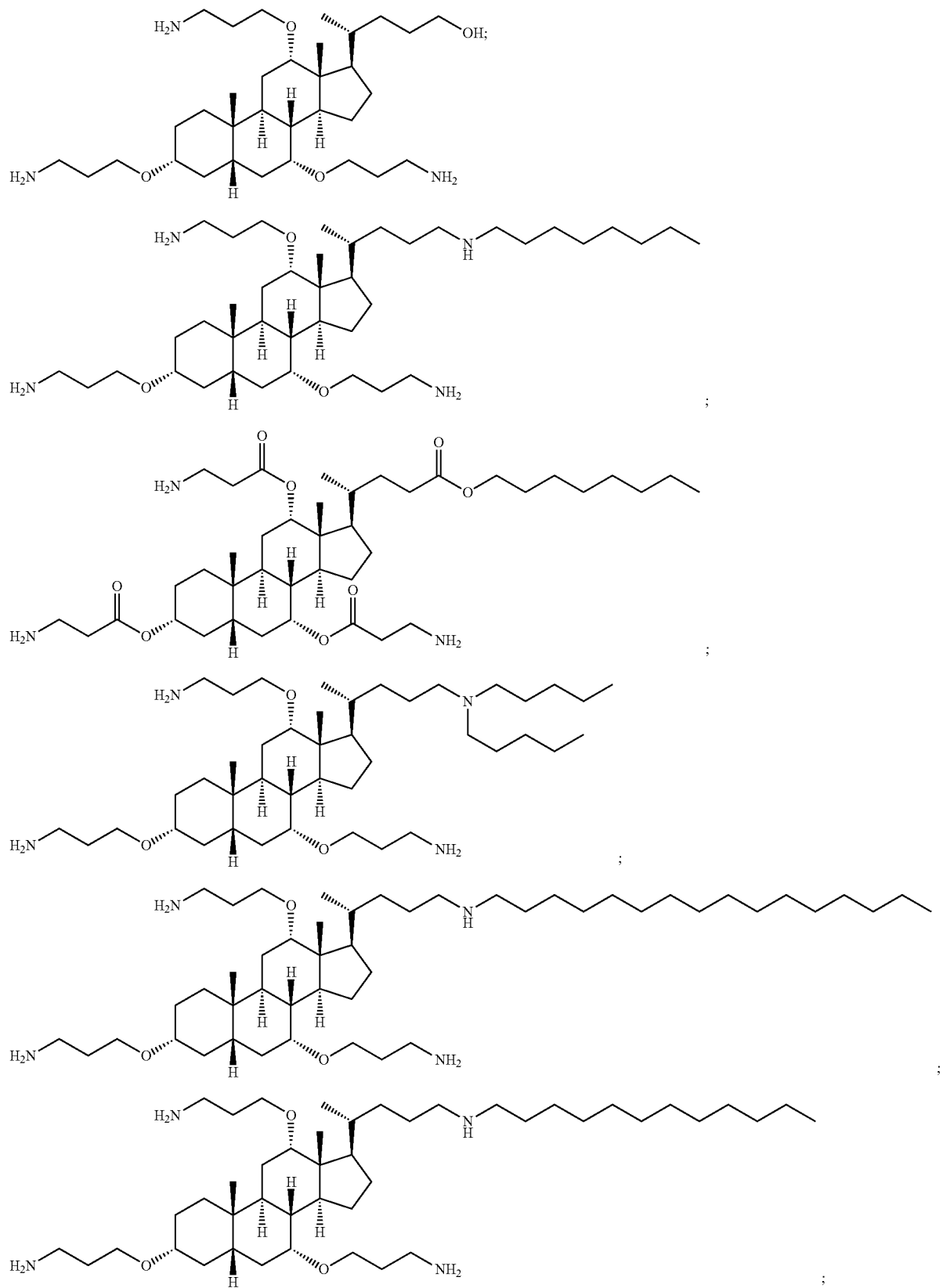

-continued

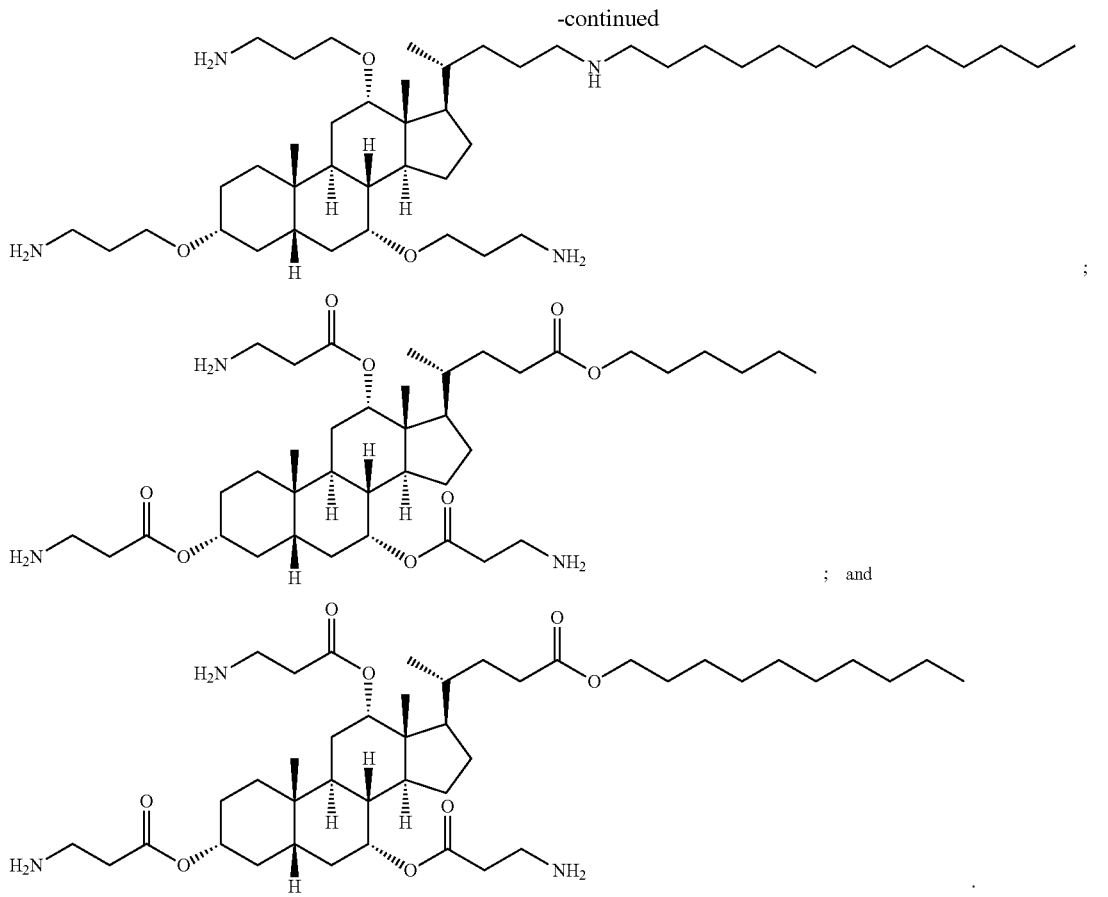

In some embodiments, the compounds or salts thereof are selected from the compound of Formula (II), which is related to, but not identical to, Formula (I), e.g., in that $R_{18}$, rather than $R_{15}$, is optional and can be omitted:

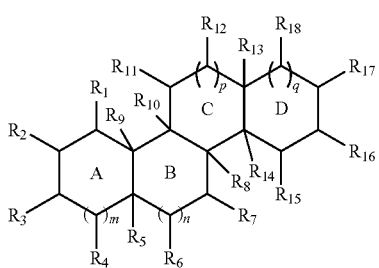

(II)

wherein
rings A, B, C, and D are independently saturated, or are fully or partially unsaturated, provided that at least two of rings A, B, C, and D are saturated;

m, n, p, and q are independently 0 or 1;

each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—$HC(Q_5)$-$C(O)$—$O$, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, ($C_1$-$C_{10}$) quaternary ammonium alkylcarboxy, and ($C_1$-$C_{10}$) guanidinoalkyl carboxy, where $Q_5$ is a side chain of any amino acid (including a side chain of glycine, i.e., H), P.G. is an amino protecting group; and each of $R_5$, $R_8$, $R_9$, $R_{10}$, $R_{13}$, and $R_{14}$ may be independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy -($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—$HC(Q_5)$-$C(O)$—$O$—, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, and ($C_1$-$C_{10}$) guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1-C_{10})$ aminoalkyl, a substituted or unsubstituted $(C_1-C_{10})$ aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino$(C_1-C_{10})$ alkyl, a substituted or unsubstituted $(C_1-C_{10})$ aminoalkyloxy-$(C_1-C_{10})$ aminoalkylaminocarbonyl, a substituted or unsubstituted $(C_1-C_{10})$ aminoalkylaminocarbonyl, a substituted or unsubstituted $(C_1-C_5)$ aminoalkylcarboxyamido, a $(C_1-C_{10})$ quaternary ammonium alkylcarboxy, $H_2N\text{—}HC(Q_5)\text{-}C(O)\text{—}O\text{—}$, $H_2N\text{—}HC(Q_5)\text{-}C(O)\text{—}N(H)\text{—}$, $(C_1-C_{10})$ azidoalkyloxy, $(C_1-C_{10})$ cyanoalkyloxy, P.G.-HN—$HC(Q_5)\text{-}C(O)\text{—}O\text{—}$, $(C_1-C_{10})$ guanidinoalkyloxy, and a $(C_1-C_{10})$ guanidinoalkylcarboxy.

In Formula (II), at least two or three of $R_3$, $R_7$, or $R_{12}$ may independently include a cationic moiety attached to the Formula (II) structure via a hydrolysable linkage. Optionally, a tail moiety may be attached to Formula (II) at $R_{17}$. The tail moiety may be charged, uncharged, polar, non-polar, hydrophobic, amphipathic, and the like. Although not required, at least two or three of m, n, p, and q can be 1. In a preferred embodiment, m, n, and p=1 and q=0.

In some embodiments, the compound of Formula (II) or pharmaceutically acceptable salt can be represented by Formula (IIA), which is a subgenus of Formula (II) in that $R_{18}$ is omitted:

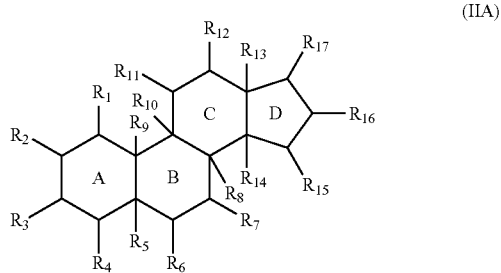

(IIA)

wherein
fused rings A, B, C, and D are independently saturated or fully or partially unsaturated;

each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, $(C_1-C_{10})$ alkylcarboxy-$(C_1-C_{10})$ alkyl, $C_1-C_{10}$ alkylamino-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkyl, a substituted or unsubstituted aryl, a substituted or unsubstituted arylamino-$(C_1-C_{10})$ alkyl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkyloxy-$(C_1-C_{10})$ alkyl, a substituted or unsubstituted $(C_1-C_{10})$ aminoalkylcarboxy, a substituted or unsubstituted $(C_1-C_{10})$ aminoalkylaminocarbonyl, a substituted or unsubstituted $(C_1-C_{10})$ aminoalkylcarboxyamido, $H_2N\text{—}HC(Q5)\text{-}C(O)\text{—}O\text{—}$, $H_2N\text{—}HC(Q_5)\text{-}C(O)\text{—}N(H)\text{—}$, $(C_1-C_{10})$ azidoalkyloxy, $(C_1-C_{10})$ cyanoalkyloxy, P.G.-HN—$HC(Q_5)\text{-}C(O)\text{—}O\text{—}$, $(C_1-C_{10})$ guanidinoalkyloxy, $(C_1-C_{10})$ quaternary ammonium alkylcarboxy, and $(C_1-C_{10})$ guanidinoalkyl carboxy, where $Q_5$ is a side chain of any amino acid (including the side chain of glycine, i.e., H), PG. is an amino protecting group;

$R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, a substituted or unsubstituted $(C_1-C_{10})$ aminoalkyl, a substituted or unsubstituted aryl, $C_1-C_{10}$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkylcarboxy, a substituted or unsubstituted $(C_1-C_{10})$ aminoalkylaminocarbonyl, $H_2N\text{—}HC(Q_5)\text{-}C(O)\text{—}O\text{—}$, $H_2N\text{—}HC(Q_5)\text{-}C(O)\text{—}N(H)\text{—}$, $(C_1-C_{10})$ azidoalkyloxy, $(C_1-C_{10})$ cyanoalkyloxy, P.G.-HN—$HC(Q_5)\text{-}C(O)\text{—}O\text{—}$, $(C_1-C_{10})$ guanidinoalkyloxy, and $(C_1-C_{10})$ guanidinoalkylcarboxy, where $Q_5$ is a side chain of any amino acid, PG. is an amino protecting group; and at least two of $R_1$ through $R_{14}$ are independently selected from the group consisting of a substituted or unsubstituted $(C_1-C_{10})$ aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino$(C_1-C_{10})$ alkyl, a substituted or unsubstituted $(C_1-C_{10})$ aminoalkyloxy-$(C_1-C_{10})$ alkyl, a substituted or unsubstituted $(C_1-C_{10})$ aminoalkylaminocarbonyl, $(C_1-C_{10})$ quaternary ammonium alkylcarboxy, $H_2N\text{—}HC(Q_5)C(O)\text{—}O\text{—}$, $H_2N\text{—}HC(Q_5)\text{-}C(O)\text{—}N(H)\text{—}$, $(C_1-C_{10})$ azidoalkyloxy, $(C_1-C_{10})$ cyanoalkyloxy, PG.-HN—$HC(Q_5)\text{-}C(O)\text{—}O\text{—}$, $(C_1-C_{10})$ guanidinoalkyloxy, and $(C_1-C_{10})$ guanidinoalkylcarboxy.

While not required, the cationic cholesterol compounds can be pharmaceutically acceptable salts of any of the cationic cholesterol additives described herein. In some embodiments, the pharmaceutically acceptable salt is a hydrochloride salt. In some embodiments, the pharmaceutically acceptable salt is a tri-hydrochloride salt.

While not required, the compound preferably has low bioavailability. The bioavailability is preferably less than 50%, 20%, 10%, or 1% in water and/or in the drinking water and/or feed composition used to deliver the cationic cholesterol additive.

In some embodiments, compounds comprise a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group.

The compound can also contain a hydrophobic group. In some embodiments, the hydrophobic group is a substituted $(C_3-C_{10})$ aminoalkyl group, a $(C_1-C_{10})$ alkyloxy $(C_1-C_{10})$ alkyl group, or a $(C_1-C_{10})$ alkylamino $(C_3-C_{10})$ alkyl group, attached to the steroid backbone. In some embodiments, the hydrophobic group is a substituted, branched, or unbranched substituent with greater than 12, 16, 18, 20, or 22 carbons. In some embodiments, the hydrophobic group may include a hydrocarbon chain of at least 9, 11, or 13 carbons distal to a heteroatom. In some embodiments, a compound having a structure according to Formula (I) includes a hydrophobic group at $R_{18}$.

In some embodiments, the compounds set forth herein preserve certain stereochemical and electronic characteristics found in steroids. The term "same configuration" as used herein refers to substituents on the fused steroid having the same stereochemical orientation. For example, in some embodiments, substituents $R_3$, $R_7$ and $R_{12}$ are all 13-substituted or a-substituted.

In some embodiments, compounds include, but are not limited to, compounds having amine or guanidine groups covalently attached to a steroid backbone or scaffold at any carbon position, e.g., cholic acid. In various embodiments, a group is covalently attached at any one, or more, of positions $C_3$, $C_7$ and $C_{12}$ of the steroid backbone or scaffold. In additional embodiments, a group is absent from any one, or more, of positions $C_3$, $C_7$ and $C_{12}$ of the steroid backbone or scaffold. Compounds that include such groups can include a tether, the tether having variable chain length or size. As used herein, the terms "tether" or "tethered," when used in reference to a compound, refers to the chain of atoms between the steroid backbone or scaffold and a terminal amino or guanidine group. In various embodiments, a tether is covalently attached at anyone, or more, of positions $C_3$, $C_7$ and $C_{12}$. In additional embodiments, a tether is lacking at anyone, or more, of positions $C_3$, $C_7$ and $C_{12}$. A tether length may include the heteroatom (O or N) covalently attached to the steroid backbone. The tether may include a hydrolysable linkage such as an ester linkage.

In some embodiments, other ring systems can also be used, e.g., 5-member fused rings. Compounds with backbones having a combination of 5- and 6-membered rings are also contemplated. Amine or guanidine groups can be separated from the backbone by at least one, two, three, four or more atoms. The backbone can be used to orient the amine or guanidine groups on one face, or plane, of the steroid. For example, a scheme showing a compound having primary amino groups on one face, or plane, of a backbone is shown in Scheme I above.

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound.

IV. Feed Compositions

The feed compositions are prepared by selecting suitable feed components for formulating a feed for a particular type of animal and adding an effective amount of cationic cholesterol compound for enhancing the health and reducing the morbidity of the animal. The feed component can be solid or liquid. The feed component can be animal food that provides calories and nutrients or it may be drinking water.

Suitable effective amounts of cationic cholesterol compounds in a feed composition includes concentrations of the cationic cholesterol additive of at least 0.0001%, 0.01%, 0.1%, 1.0% by weight and/or less than 5%, 1%, or 0.1%, 0.01 and/or within a range of the foregoing. In some embodiments, the cationic cholesterol compounds may be included in a fluid. The concentration may be at least 0.5 ppm, 1 ppm, 2 ppm, 5 ppm, 10 ppm and/or less than 1000 ppm, 500 ppm, 100 ppm, 50 ppm, or ppm, or within a range of any of the foregoing concentrations.

The feed composition may be formulated to provide proper nutrients to an animal selected from the group of cattle, horses, poultry, sheep, or swine.

The cationic cholesterol additive may be any of the cationic cholesterol additives described herein or a combination of these. The cationic cholesterol additive may have cationic groups attached to the sterol group through a hydrolysable ester linkage. An ester linkage may allow for the compound to degrade into cholesterol and an amine compound.

V. Methods and Uses

Methods disclosed herein include treating agricultural animals with a cationic cholesterol additive. The method may include providing feed to an animal with an effective amount of a cationic cholesterol compound for enhancing health and growth of the animal. The feed composition may be administered orally in the feed (wet or dry), include solid foods, slurries, solutions, dispersions, and/or drinking water of the animal. The administration may be periodically or continuously throughout the growth of the animal to maturity or at periods throughout the growth of the animal. The compound can be administered in the feed through a regular feeding. "Feeding" includes eating and/or drinking.

In some embodiments, the cationic cholesterol additive is administered at least once every 10 days, 5 days, 2 days, or 1 day for a period of at least 1 month, 2 months, or 3 months, or 6 months. The cationic cholesterol additive may be administered in at least 25%, 50%, 75% or 90% of the feedings of the animal for at least 25%, 50%, 75%, or 90% of the animal's growth to maturity or during its life time or even in substantially all of the animal's food or drinking water.

The methods are particularly advantageous for confined animal feed operations. In some embodiments, the method is carried out where the number of animals in the feeding operation is at least 250 beef; 150 dairy cattle; 500 swine; 100 horses; 2,000 sheep or lambs; 5,000 turkeys; or 5,000 chickens. In another embodiment the number of animals may be at least 500 beef; 300 dairy cattle; 1000 swine; 200 horses; 4,000 sheep or lambs; 10,000 turkeys; or 10,000 chickens.

The compositions and methods can reduce harmful bacteria in the digestive tract of an animal (e.g., *e. coli, salmonella*, or bacteria that may cause or aggravate hepatitis), increase beneficial bacteria flora (e.g., *lactobacillus*), improve feed conversion efficiency, reduce morbity and/or mortality, and/or yield harvested meat having reduced content of harmful bacteria. Unexpectively, cationic cholesterol molecules have been shown to be selective toward killing harmful bacterial instead of beneficial bacteria, i.e., because the minimum inhibitory concentration (MIC) of cationic cholesterol molecules required to kill harmful bacterial is substantially lower, e.g., an order of magnitude lower, than the MIC required to kill beneficial bacteria. By way of example, the MIC for harmful bacteria can be 1-3 ppm, while the MIC for beneficial bacteria can be 50 ppm or more. A postulated reason may be that bacteria that make up beneficial digestive trace flora have, by evolution, adapted to molecules such as cholesterol that are commonly found in animal cells, including cells in the digestive tract, while harmful bacteria have not been able to adapt as well to such molecules.

The ability of the cationic cholesterol molecules to kill harmful bacteria in the digestive track provides animals with improved health. Moreover, when an animal is harvested for meat, the decreased quantity of harmful bacteria in the digestive track of the slaughtered animal would be expected to reduce the content of harmful bacteria in the harvested meat.

By way of example, animals that normally had a feed conversion efficiency of 1.73 lbs. of feed for every 1 lb. of growth of were found to have a feed conversion efficiency of 1.63 lbs. of feed for every 1 lb. of growth when fed cationic cholesterol molecules. That represents a 6% increase in feed conversion efficiency.

VI. EXAMPLES

Example 1

Decreased Morbidity of Chickens

A study of 50,000 birds performed in 2 groups of 25,000 birds was performed on a confined animal feed operation. The following cationic cholesterol additive (CSA-44) was added to animal drinking water:

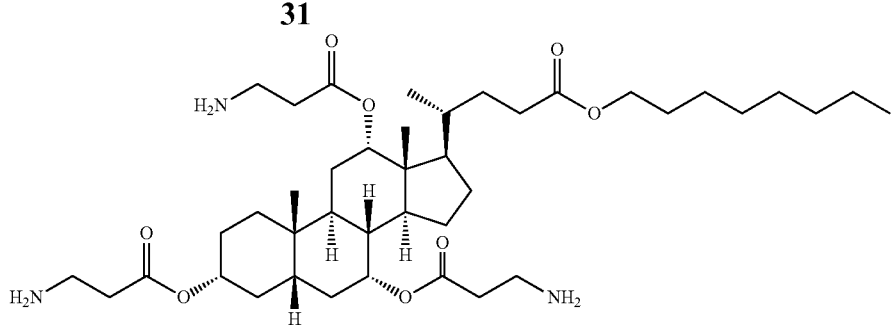

The additive was prepared in drinking water at a concentration of 5 ppm. The dry feed administered to the chickens contained no antibiotic.

A control group of birds was delivered tetracycline in animal feed according to conventional practices.

The cationic cholesterol additive was given from day one through day 35. Death loss went from an average of 1400-1500 birds in the control group to 535 with the cationic cholesterol additive. Weight gain for the birds fed with the additive improved from 0.112 lbs per day to 0.120 lbs per day and the harvest weight went from 3.85 lbs to 4.22 lbs. In addition, feed conversion efficiency was improved by 8%. That means the animals more efficiently utilized the feed, which could reduce feed costs and/or result in healthier animals. Accordingly, some embodiments described herein are directed to methods/processes of improving feed conversion efficiency. The improved health and weight gain of the birds using the cholesterol additive is surprising and unexpected given the absence of tetracycline in the feed as compared to the control, which included tetracycline.

Example 2

Effect of Cationic Cholesterol Compound on Mortality & Morbidity of Animal in a *C. difficile* Challenge Model

*Clostridium difficile*-associated diseases (e.g. antimicrobic-associated diarrhea and pseudomembranous colitis) are usually nosocomial in origin and result in excessive morbidity and mortality among hospitalized patients. There has been a significant increase in the incidence and severity of *C. difficile*-associated diarrhea (CDAD) in the past several years. Current guidelines recommend treatment with metronidazole. Recently, a new, highly virulent strain of *C. difficile* has appeared that is less responsive to standard therapy and is associated with a high rate of recurrence.

To evaluate the effectiveness of cationic cholesterol compounds on GI microbiota, the following compound (CSA-44) was administered oraly by gastric lavage to mice at 10 mg/kg:

To determine the health improvements caused by the cationic cholesterol compound, the concentration (cfu/mL) of *Lactobacillus* bacteria (LAB) (beneficial flora) in the ileum, cecum, and colon was determined at 12 and 24 hours. The LAB concentration was compared to control mice.

Figure 2:
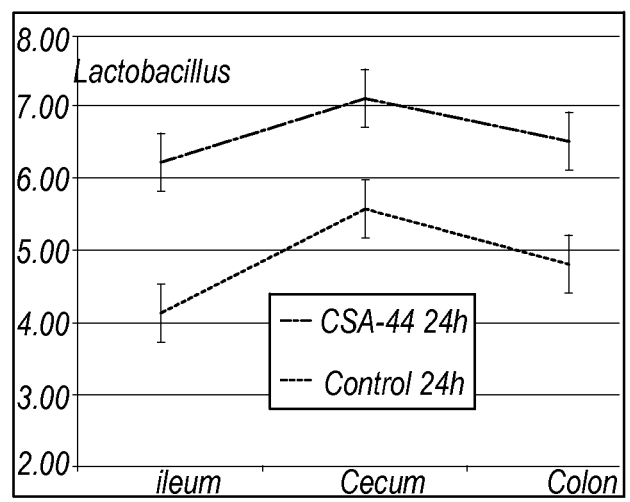
FIG. 2 is a graph showing the effect of CSA-44 on beneficial bacterial flora in the digestive tract of mice.

As illustrated in the graphs of FIGS. 1 and 2, the cationic cholesterol compound appears to have a significant "sparing" effect on beneficial *Lactobacillus* bacteria (LAB) flora (log values on y-axis) in the ileum, cecum and colon (on x-axis) when compared to control mice at 12 and 24 hours after being given CSA-44 ("post Tx"), resulting in almost a 2 log increase in LAB concentration in all 3 segments of the intestine when compared to control mice. This increase in LAB concentration flora is a surprising and unexpected result. These results also suggest a mechanism by which the chicken morbidity rate was decreased in the study described in Example 1. It also suggests that the MIC for beneficial bacteria such as LAB is substantially higher than the MIC for harmful bacteria such as *C. difficile*.

Figure 3:
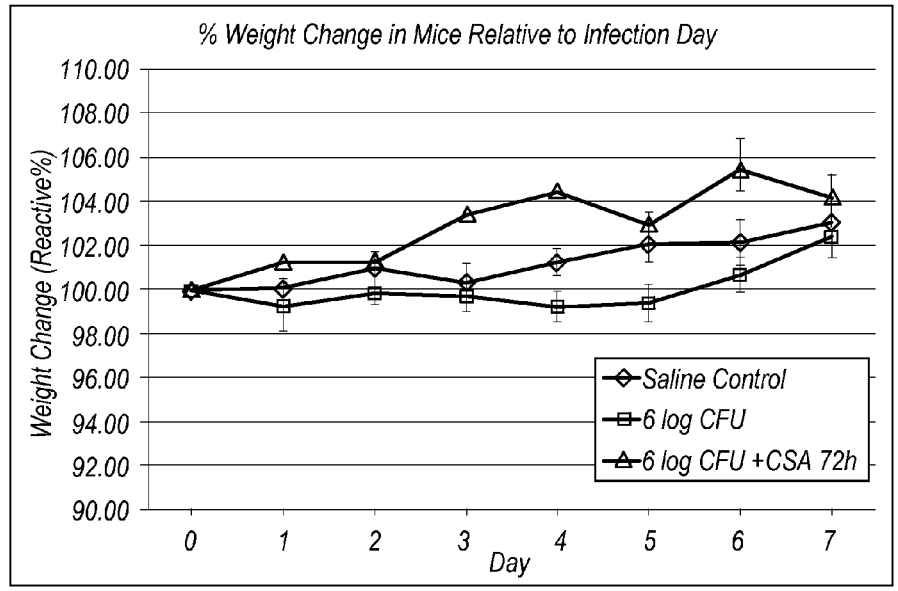
FIG. 3 is a graph showing the effect of CSA-44 on weight gain of mice infected with harmful bacteria.

In another study with the mice of Example 2, a cationic cholesterol additive was administered to determine changes in weight gain. The compound was administered orally @10/mg/kg once, 24 and 48 hours after *C. difficile* ATCC 9689 challenge at 1×10⁵ cfu (or CFU) or 72 hours after challenge with 1×10⁶ cfu (or CFU) (Day 0). The results are illustrated in the graph of FIG. 3. While not statistically different, there was a trend for the treated mice to have greater weight gain after challenge with *C. difficile*.

Figure 4:
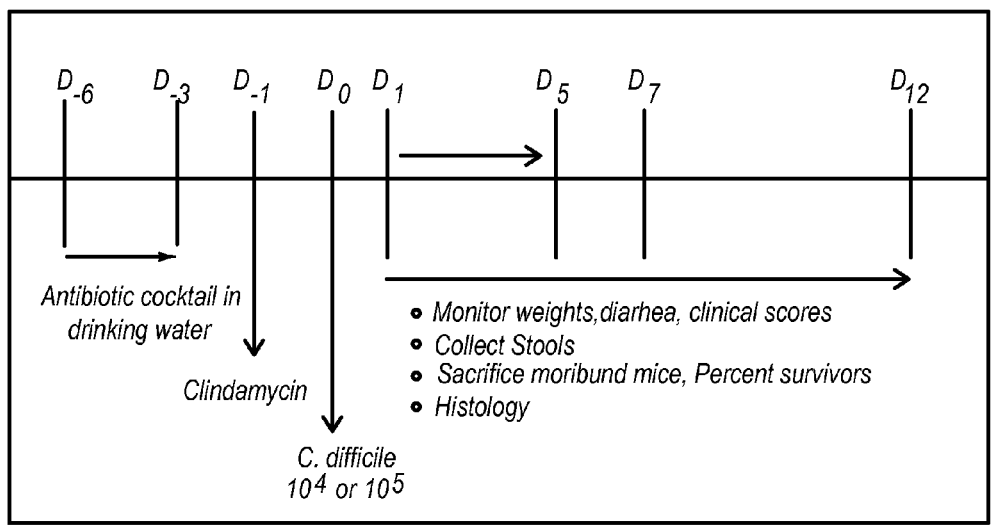
FIG. 4 illustrates a study designed to show the effect of administering CSA-44 on the morbidity of mice infected with *C. difficile*.
Figure 5:
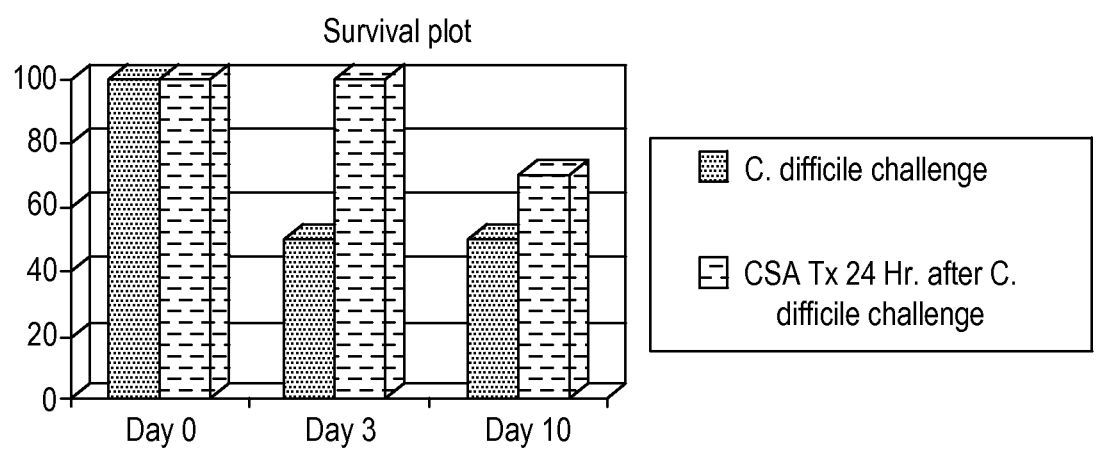
FIG. 5 is a graph showing the effect of CSA-44 on the mortality of mice infected with harmful bacteria.

The mice of Example 2 were also evaluated for decreased morbidity in an LD₅₀ *C. difficile* challenge model. The cationic cholesterol compound was administered 24 hours after *C. difficile* challenge ("Tx 24 Hr."). FIG. 4 illustrates the steps used in performing the study. The morbidity results shown in the graph of FIG. 5 (survival rate on y-axis; time intervals (Day 0, Day 3, Day 10) on x-axis) illustrate the improved survival rate of the challenge between mice using the cationic cholesterol compound and the control mice, which were not given the cationic cholesterol compound.

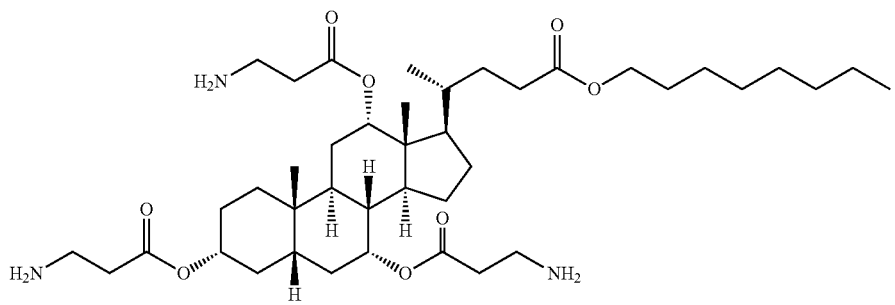

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of improving the health of an animal, comprising:
   feeding the animal a diet comprised of a cationic cholesterol additive,
   the cationic cholesterol additive including a compound having the following structure, or salt thereof:

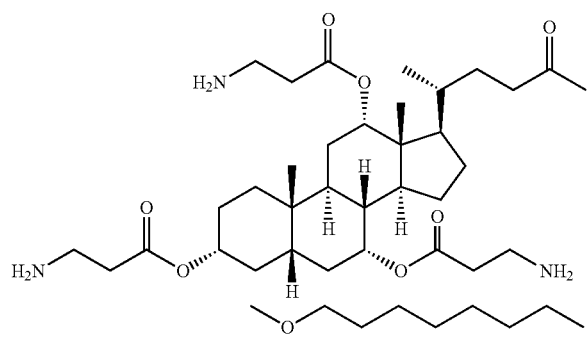

and wherein the feeding the animal a diet comprised of the cationic cholesterol additive improves feed conversion efficiency by at least 6% compared to if the animal were fed the quantity of feed in the absence of the cationic cholesterol additive.

2. A method as in claim 1, wherein the cationic cholesterol compound is fed to the animal in the food of the animal.

3. A method as in claim 2, wherein the food is a dry feed.

4. A method as in claim 1, wherein the cationoic cholesterol additive is fed to the animal in the drinking water of the animal.

5. A method as claim 1, wherein the cationic cholesterol additive is administered at least once every 10 days, for a period of at least 1 month.

6. A method as claim 1, wherein the cationic cholesterol additive is administered at least once every 5 days for a period of at least 2 months.

7. A method as claim 1, wherein the cationic cholesterol additive is administered at least once every 2 days for a period of at least 3 months.

8. A method as claim 1, wherein the cationic cholesterol additive is administered in at least 25% of the feedings of the animal for at least 25% of the animal's growth to maturity or during its life time.

9. A method as claim 1, wherein the cationic cholesterol additive is administered in at least 50% of the feedings of the animal for at least 50% of the animal's growth to maturity or during its life time.

10. A method as in claim 1, wherein the cationic cholesterol additive is included in a concentration of at least 0.0001% by weight of a feed composition containing the cationic cholesterol additive fed to the animal and/or less than 5% by weight of the feed composition or within a range of the foregoing.

11. A method as in claim 1, wherein the cationic cholesterol additive is included in a concentration of at least 0.01% by weight of a feed composition containing the cationic cholesterol additive fed to the animal and/or less than 1% by weight of the feed composition or within a range of the foregoing.

12. A method as in claim 1, wherein the cationic cholesterol compound is included in a concentration of at least 0.5 ppm of a feed composition containing the cationic cholesterol additive fed to the animal and/or less than 1000 ppm of the feed composition, or within a range of the foregoing.

13. A method as in claim 1, wherein the cationic cholesterol compound is included in a concentration of at least 2 ppm of a feed composition containing the cationic cholesterol additive fed to the animal and/or less than 500 ppm of the feed composition, or within a range of the foregoing.

14. A method as in claim 1, wherein the animal is selected from the group consisting of cattle, poultry, sheep, swine, and combinations thereof.

15. A method as in claim 1, wherein the animal is raised in a confined animal feed operation.

16. A method as in claim 15, wherein the confined animal feed operation includes at least 250 beef, at least 150 dairy cattle, at least 500 swine, at least 100 horses, at least 2,000 sheep or lambs, at least 5,000 turkeys, and/or at least 5,000 chickens.

17. A method as in claim 1, wherein the cationic cholesterol additive kills bacteria in the digestive track of the animal.

18. A method as in claim 17, wherein the animal, when slaughtered, yields harvested meat having a reduced content of harmful bacteria.

19. A method of improving the health of an animal, comprising:
   feeding the animal a diet comprised of a cationic cholesterol additive,
   the cationic cholesterol additive including a compound having the following structure, or salt thereof:

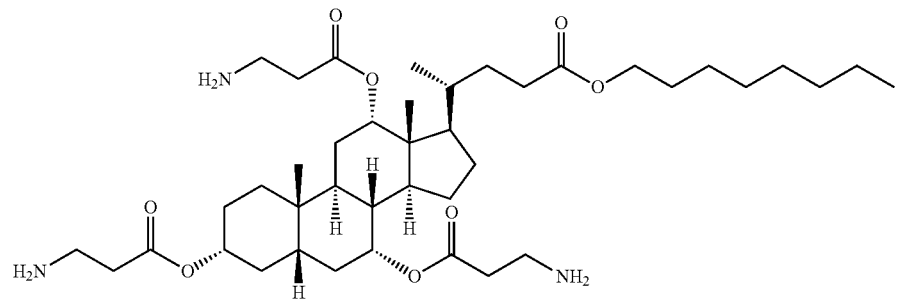

and wherein the feeding the animal a diet comprised of the cationic cholesterol additive selectively kills *C. difficile*, while maintaining or enhancing growth of *lactobacillus*, in the gastrointestinal tract of the animal.

20. A method as in claim 19, wherein the cationic cholesterol additive improves feed conversion efficiency by the animal when fed a quantity of feed.

21. A method as in claim 20, wherein the cationic cholesterol additive improves feed conversion efficiency by at least 6% compared to if the animal were fed the quantity of feed in the absence of the cationic cholesterol additive.

22. A method as in claim 20, wherein the cationic cholesterol additive improves feed conversion efficiency compared to if the animal were fed the quantity of feed and an antibiotic instead of the cationic cholesterol additive.

* * * * *